(12) United States Patent
Organ et al.

(10) Patent No.: US 7,125,571 B2
(45) Date of Patent: Oct. 24, 2006

(54) HERBAL FORMULATION

(75) Inventors: Eric J. Organ, Kinnelon, NJ (US); Denise L. Organ, Kinnelon, NJ (US)

(73) Assignee: D & E Pharmaceuticals, Inc., Bloomingdale, NJ (US)

( * ) Notice: Subject to any disclaimer, the term of this patent is extended or adjusted under 35 U.S.C. 154(b) by 0 days.

(21) Appl. No.: 10/991,744

(22) Filed: Nov. 18, 2004

(65) Prior Publication Data

US 2005/0112212 A1 May 26, 2005

Related U.S. Application Data

(60) Provisional application No. 60/524,815, filed on Nov. 25, 2003.

(51) Int. Cl.
*A61K 36/00* (2006.01)

(52) U.S. Cl. ........................ 424/725; 424/776

(58) Field of Classification Search ............... 424/725, 424/776
See application file for complete search history.

(56) References Cited

U.S. PATENT DOCUMENTS

| | | | |
|---|---|---|---|
| 6,203,819 B1 * | 3/2001 | Fine ........................ 424/646 |
| 6,485,760 B1 | 11/2002 | Matsuyama | |
| 6,503,529 B1 * | 1/2003 | Fleischner ............... 424/439 |
| 6,551,627 B1 * | 4/2003 | Yoon et al. ............... 424/725 |
| 6,716,459 B1 | 4/2004 | Matsuyama | |
| 6,784,206 B1 | 8/2004 | Udell et al. | |
| 6,787,163 B1 * | 9/2004 | Harris et al. ............. 424/725 |
| 2002/0012708 A1 * | 1/2002 | Ruepp ..................... 424/725 |
| 2002/0018818 A1 * | 2/2002 | Suzuki et al. ............ 424/725 |
| 2004/0105908 A1 * | 6/2004 | Suzuki et al. ............ 424/776 |
| 2005/0048144 A1 * | 3/2005 | Han et al. ................ 424/732 |

FOREIGN PATENT DOCUMENTS

JP 05310587 A * 11/1993
JP 2003034636 A * 2/2003

OTHER PUBLICATIONS

Internet website http://healthyherbs.about.com/cs/herbsfaqs/a/aa030602_p.htm (1 page only).*
Internet website http://www.ibiblio.org/pfaf/cgi-bin/arr_html?Galega+officinalis (5 pages total).*
Internet website http://www.itmonline.org/arts/coffee.htm (10 pages total).*
Internet website "Herbal Monograph- *Pterocarpus marsupium*" (2002) (1 page total).*

* cited by examiner

*Primary Examiner*—Christopher R. Tate
*Assistant Examiner*—S. B. McCormick-Ewoldt
(74) *Attorney, Agent, or Firm*—Fraser Martin & Miller LLC; Donald R. Fraser

(57) ABSTRACT

An herbal formulation comprises green coffee bean extract, artichoke extract, banaba leaf extract, chromium polynicotinate, vanadyl sulphate, pterocarpus marsupium extract, gymnemia sylvestre extract, biotin, and goat's rue extract.

30 Claims, No Drawings

HERBAL FORMULATION

CROSS-REFERENCE TO RELATED PATENT/APPLICATION

This application claims the benefit of U.S. Provisional Patent Application Ser. No. 60/524,815 filed on Nov. 25, 2003.

FIELD OF THE INVENTION

The present invention relates generally to an herbal formulation. More particularly, the invention is directed to an herbal formulation, which may be effective for suppressing glucose production in the human body.

BACKGROUND OF THE INVENTION

Compounds which are effective for suppressing the production of glucose in the human body may additionally be beneficial to those suffering from diabetes and conditions which are precursors to diabetes. Diabetes mellitus (diabetes) is broadly defined as a group of metabolic diseases caused by defects in insulin secretion and/or insulin action resulting in hyperglycemia. Diabetes has been identified as the fifth leading cause of disease death in the United States. Of particular concern are the increasing rates of previously rare type 2 diabetes in children and adolescents.

People with diabetes have a higher morbidity rate than the general population, as well as higher risks for heart disease, blindness, kidney failure, extremity amputation, and other chronic conditions. The causes of diabetes are associated with several pathogenic processes including autoimmune destruction of cells in the pancreas, resulting in insulin deficiency, metabolic abnormalities that result in resistance to insulin action, or both. Diabetes is generally divided into two categories. Type 1 diabetes is caused by an autoimmune defect resulting in an absolute deficiency of insulin secretion. A resistance to insulin action combined with an inadequate compensatory insulin secretion response causes type 2 diabetes.

Symptoms of diabetes include polyuria, polydipsia, weight loss, polyphagia, blurred vision, hypertension, abnormalities of lipoprotein metabolism, and periodontal disease. Diabetes can lead to impaired growth and susceptibility to certain types of infections. Over the long-term, diabetes can also lead to: reinopathy with blurred vision; nephropathy resulting in renal failure; peripheral neuropathy resulting in foot ulcers, amputation, and Charcot joints; and autonomic neuropathy causing gastrointestinal, genitourinary, and cardiovascular symptoms and secual dysfunction.

Moreover, there are a number of precursors to diabetes which also can be debilitating. Pre-diabetes, for example, is a condition wherein blood glucose levels are higher than normal, but not yet high enough to be diagnosed as diabetes. Pre-diabetes may result in long term damage to the body, especially to the heart and circulatory system. Research has demonstrated that action taken to control blood glucose levels for one having pre-diabetes can prevent the onset of type 2 diabetes.

Likewise, Syndrome X (also referred to as Metabolic Syndrome), a possible precursor to diabetes, may result in an increased risk of coronary artery disease. Syndrome X comprises three or more of the conditions of glucose intolerance, high blood pressure, high blood triglycerides, low levels of HDL, and abdominal obesity. Reducing the body's production of glucose may reverse the likelihood that Syndrome X would develop into type 2 diabetes.

It would be desirable to develop an herbal formulation which may be effective in suppressing the production of glucose in the human body, and could also benefit those suffering from diabetes and precursor conditions.

SUMMARY OF THE INVENTION

Accordant with the present invention, an herbal formulation, which may suppress the production of glucose in the human body, has surprisingly been discovered. The inventive herbal formulation comprises green coffee bean extract, artichoke extract, banaba leaf extract, chromium polynicotinate, vanadyl sulphate, pterocarpus marsupium extract, gymnemia sylvestre extract, biotin, and goat's rue extract.

The herbal formulation according to the present invention is useful as a food supplement, and additionally may assist the suppression of glucose production in the human body.

DETAILED DESCRIPTION OF THE PREFERRED EMBODIMENT

The present invention is directed to an herbal formulation, comprising green coffee bean extract, artichoke extract, banaba leaf extract, chromium polynicotinate, vanadyl sulphate, pterocarpus marsupium extract, gymnemia sylvestre extract, biotin, and goat's rue extract.

Green coffee bean extract is a well-known stimulant and diuretic. Green coffee bean extract may be present in the inventive formulation at a concentration up to about 70 weight percent. Preferably, the concentration is up to about 35 weight percent.

Artichoke extract is a well-known digestive aid and diuretic. Artichoke extract may be present in the inventive formulation at a concentration up to about 70 weight percent. Preferably, the concentration is up to about 35 weight percent.

banaba leaf extract is a well-known appetite suppressant. banaba leaf extract may be present in the inventive formulation at a concentration up to about 10 weight percent. Preferably, the concentration is up to about 5 weight percent.

Chromium polynicotinate is a well-known compound which helps to metabolize fat and protein in the human body. Chromium polynicotinate may be present in the inventive formulation at a concentration up to about 0.001 weight percent. Preferably, the concentration is up to about 0.0005 weight percent.

Vanadyl sulphate is a well-known compound which aids cellular metabolism. Vanadyl sulphate may be present in the inventive formulation at a concentration up to about 70 weight percent. Preferably, the concentration is up to about 35 weight percent.

Pterocarpus marsupium extract is a well-known astringent and antiseptic. Pterocarpus marsupium extract may be present in the inventive formulation at a concentration up to about 70 weight percent. Preferably, the concentration is up to about 35 weight percent.

Gymnemia sylvestre extract is a well-known compound used to assist metabolism. Gymnemia sylvestre extract may be present in the inventive formulation at a concentration up to about 70 weight percent. Preferably, the concentration is up to about 35 weight percent.

Biotin is a well-known compound which aids the transformation of blood glucose into energy. Biotin may be present in the inventive formulation at a concentration up to about 2 weight percent. Preferably, the concentration is up to about 1 weight percent.

Finally, goat's rue extract is a well-known diuretic and diaphoretic. Goat's rue extract may be present in the inventive formulation at a concentration up to about 70 weight percent. Preferably, the concentration is up to about 35 weight percent.

The aforementioned ingredients may be mixed together by any conventional dry blending process, and formed by conventional processes into tablets for subsequent oral administration. Alternatively, the mixed ingredients may be placed in gelatin capsules. The inventive formulation may also contain conventional food supplement adjuvants, fillers, extenders, and the like.

Conveniently, the inventive formulation may be taken orally in a wide range of dosages. The daily dosage, which may be divided for oral administration any number of times during a twenty-four hour period, ranges up to about 5 grams. Preferably, the daily dosage is about 2 grams. Alternatively, the inventive formulation may be administered to the human body by the ingestion of soft gel capsules, powder drinks, or nutritional bars, or by absorption through the skin via dermal patches.

The invention is more easily comprehended by reference to specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. An herbal formulation, comprising:
   green coffee bean extract;
   artichoke extract;
   banaba leaf extract;
   chromium polynicotinate;
   vanadyl sulphate;
   pterocarpus marsupium extract;
   gymnemia sylvestre extract;
   biotin; and
   goat's rue extract.

2. The herbal formulation according to claim 1, wherein the green coffee bean extract is present in an amount up to about 70 weight percent.

3. The herbal formulation according to claim 2, wherein the green coffee bean extract is present in an amount up to about 35 weight percent.

4. The herbal formulation according to claim 1, wherein the artichoke extract is present in an amount up to about 70 weight percent.

5. The herbal formulation according to claim 4, wherein the artichoke extract is present in an amount up to about 35 weight percent.

6. The herbal formulation according to claim 1, wherein the banaba leaf extract is present in an amount up to about 10 weight percent.

7. The herbal formulation according to claim 6, wherein the banaba leaf extract is present in an amount up to about 5 weight percent.

8. The herbal formulation according to claim 1, wherein the chromium polynicotinate is present in an amount up to about 0.001 weight percent.

9. The herbal formulation according to claim 8, wherein the chromium polynicotinate is present in an amount up to about 0.0005 weight percent.

10. The herbal formulation according to claim 1, wherein the vanadyl sulphate is present in an amount up to about 70 weight percent.

11. The herbal formulation according to claim 10, wherein the vanadyl sulphate is present in an amount up to about 35 weight percent.

12. The herbal formulation according to claim 1, wherein the pterocarpus marsupium extract is present in an amount up to about 70 weight percent.

13. The herbal formulation according to claim 12, wherein the pterocarpus marsupium extract is present in an amount up to about 35 weight percent.

14. The herbal formulation according to claim 1, wherein the gymnemia sylvestre extract is present in an amount up to about 70 weight percent.

15. The herbal formulation according to claim 14, wherein the gymnemia sylvestre extract is present in an amount up to about 35 weight percent.

16. The herbal formulation according to claim 1, wherein the biotin is present in an amount up to about 2 weight percent.

17. The herbal formulation according to claim 16, wherein the biotin is present in an amount up to about 1 weight percent.

18. The herbal formulation according to claim 1, wherein the goat's rue extract is present in an amount up to about 70 weight percent.

19. The herbal formulation according to claim 18, wherein the goat's rue extract is present in an amount up to about 35 weight percent.

20. An herbal formulation comprising:
    up to about 70 weight percent green coffee bean extract;
    up to about 70 weight percent artichoke extract;
    up to about 10 weight percent banaba leaf extract;
    up to about 0.001 weight percent chromium polynicotinate
    up to about 70 weight percent vanadyl sulphate;
    up to about 70 weight percent pterocarpus marsupium extract;
    up to about 70 weight percent gymnemia sylvestre extract;
    up to about 2 weight percent biotin; and
    up to about 70 weight percent goat's rue extract.

21. The herbal formulation according to claim 20, wherein the green coffee bean extract is present in an amount up to about 35 weight percent.

22. The herbal formulation according to claim 20, wherein the artichoke extract is present in an amount up to about 35 weight percent.

23. The herbal formulation according to claim 20, wherein the banaba leaf extract is present in an amount up to about 5 weight percent.

24. The herbal formulation according to claim 20, wherein the chromium polynicotinate is present in an amount up to about 0.0005 weight percent.

25. The herbal formulation according to claim 20, wherein the vanadyl sulphate is present in an amount up to about 35 weight percent.

26. The herbal formulation according to claim 20, wherein the pterocarpus marsupium extract is present in an amount up to about 35 weight percent.

27. The herbal formulation according to claim 20, wherein the gymnemia sylvestre extract is present in an amount up to about 35 weight percent.

28. The herbal formulation according to claim 20, wherein the biotin is present in an amount up to about 1 weight percent.

29. The herbal formulation according to claim 20, wherein the goat's rue extract is present in an amount up to about 35 weight percent.

30. An herbal formulation comprising:
 up to about 35 weight percent green coffee bean extract;
 up to about 35 weight percent artichoke extract;
 up to about 5 weight percent banaba leaf extract;
 up to about 0.0005 weight percent chromium polynicotinate
 up to about 35 weight percent vanadyl sulphate;
 up to about 35 weight percent pterocarpus marsupium extract;
 up to about 35 weight percent gymnemia sylvestre extract;
 up to about 1 weight percent biotin; and
 up to about 35 weight percent goat's rue extract.

* * * * *